United States Patent [19]

Bruggeman et al.

[11] Patent Number: 5,800,981
[45] Date of Patent: Sep. 1, 1998

[54] HUMAN CYTOMEGALOVIRUS ANTIGEN AND ITS USE

[75] Inventors: Catharina A. Bruggeman; Cornelis Vink, both of AZ Maastricht, Netherlands; Albert Ramon, Limberg, Belgium; Frans Stals, CV Roermond, Netherlands

[73] Assignee: University of Limburg, Maastricht, Netherlands

[21] Appl. No.: 605,541

[22] Filed: Feb. 22, 1996

[51] Int. Cl.$^6$ .............. C12Q 1/70; C12P 19/34; A61K 39/12; C07K 1/00

[52] U.S. Cl. .............. 435/5; 435/7.92; 435/7.93; 435/69.1; 435/91.1; 435/172.3; 424/186.1; 424/230.1; 424/257.1; 424/185.1; 530/350; 536/23.72; 536/23.1

[58] Field of Search .............. 435/5, 7.92, 69.1, 435/91.1, 172.3, 7.93; 424/186.1, 230.1, 185.1, 257.1; 530/350; 536/23.72, 23.1

[56] References Cited

FOREIGN PATENT DOCUMENTS 9601321 1/1996 WIPO .............. C12N 15/38

OTHER PUBLICATIONS

Landini, M. et al. 1991, J. Clin. Micro, vol. 29, No. 9, pp. 1868–1872.

Landini, M. et al, 1995, J. Clin. Micro, vol. 33, No. 10, pp. 2535–2542.

Rioalti, A. et al, 1994, J. Clin. Micro, vol. 32, No. 1, pp. 358–363.

Bevan, I.H. et al., "Polymerase chain reaction for detection of human cytomegalovirus infection in a blood donor population," Br. J. Chem. 78:94–99 (1991).

Bruggeman, C.A., "Cytomegalovirus and latency: an overview," Virchows Archiv. B. Cell Path. 64:325–33 (1993)

Collaborative DHPG Treatment and Study Group, "Treatment of serious sytomegalovirus infections with 9–(1, 3–dihydroxy–2–propoxymethyl)guanine in patients with AIDS and others immunodeficiencies", New Eng. J. Med. 314(13):801–5 (1986).

Gerna, G. et al., "Monitoring of human cytomegaloviurs infections and ganciclovir treatment in heart transplant recipients by determination of viremia, antigenemia, and DNAemia," J. Infect. Dis 164:488–98 (1991).

Goodrich, J.M. et al., "Early treatment with ganciclovir to prevent cytomegalovirus disease after allogenic bone marrow transplantation," New. Eng. J. Med. 325(23):1601–7 (1991).

Hendrix, M.G.R. et al., "The presence of cytomegalovirus nucleic acids in arterial walls of atheroslcerotic and nonatherosclerotic patients," Am. J. Path. 134(5):1151–7 (1989).

Kraat, Y.J. et al., "Comparison of four techniques for detection of antibodies of cytomegalovirus," J. Clin. Micro. 30(2):522–4 (1992).

Marsano, L. et al., "Comparison of culture and serology for the diagnosis of cytomegalovirus infection in kidney and liver transplant recipients," J. Infect. Dis. 161:454–61 (1990).

Merrigan, T.C. et al., "A controlled trial of ganciclovir to prevent cytomegalovirus disease after heart transplantation," New. Eng. J. Med. 326(18):1182–6 (1992).

Meyers, J.D. et al., "Prevention of cytomegalovirus infection by cytomeglouirus immune globulin after marrow transplantation," Ann. Int. Med. 98(4): 442–6 (1983).

Meyers, J.D. et al., "Acyclovir for prevention of cytomegalovirus infection and disease after allogenic marrow transplantation," New. Eng. Med. 318(2):70–5 (1988).

Nielsen, S.L. et al., "Kinetics of specific immunoglobulins M,E, A, and G, in cogenital primary, and secondary cytomegalovirus infection studied by antibody–capture enzyme–linked immunosorbent assay," J. Clin. Micro. 26:554–61 (1988).

Pande, H. et al., "Human cytomegalovirus strain Towne pp65 gene: nucleotide sequence and expression in *Esherichia coli*," Virol. 182:220–8 (1991).

Rubin, R.H., "Impact of cytomegalovirus infection on organ transplant recipients," Rev. Infect. Dis. 12(suppl. 7):S754–66 (1990).

Sarov, I. et al., "Detection of virus–specific IgA antibodies in serum of kidney transplant patients with recurrent cytomegalovirus infection by enzymeimmuno and radioimmunoassay techniques," Clin. Exp. Immunol. 48:321–8 (1982).

Schooley, R.T., "Cytomegalovirus in the setting of infection with human immunodeficiency virus," Rev. Infect. Dis. 12(suppl. 12):S811–19 (1990).

Smith, T.F. and Shelly, C.D., "Detection of IgM antibody to cytomegalovirus and rapid diagnosis of this virus infection by the shell viral assay." J. Virol. Methods 21:87–96 (1988).

Snydman, D.R. et al., "Use of cytomegalovirus immune globulin prevent cytomegalovirus disease in renal–transplant recipients," New Engl. J. Med. 317(17);1049–54 (1987).

Stals, F.S. et al., "Generalized cytomegalovirus (CMV) infeciton and CMV–induced pneumonitis in the rat: Combined effect of 9–(1, 3–dihydroxy–2–propoxymethyl)guanine and specific antibody treatment," Antiviral Res. 25:147–60 (1994).

Stagno, S. et al., "Immunoglobulin M antibodies detected by enzyme–linked immunosorbent assay and radioimmunoassay in the diagnosis of cytomegalovirus in pregnant women and newborn infants," J. Clin. Micro. 21(6):930–5 (1985).

(List continued on next page.)

Primary Examiner—Marian C. Knode
Assistant Examiner—Ali R. Salimi
Attorney, Agent, or Firm—Fish & Richardson P.C.

[57] ABSTRACT

A combined antigen having at least three portions of human cytomegalovirus (HCMV) proteins and characterized by an enhanced ability to bind HCMV-specific antibodies, for use in assays for the detection of HCMV-specific antibodies and as a vaccine to confer protective immunity against HCMV-mediated diseases.

7 Claims, 2 Drawing Sheets

OTHER PUBLICATIONS

Stevens, J.G., "Human herpesviruses: a consideration of the latent state," *Micro. Rev.* 53(3):318–32.

Tanaka, S. et al., "Possible role of cytomegalovirus in the pathogenesis of inflammatory aortic diseases: a preliminary report," *J. Vasc. Surg.* 16:274–9 (1992).

Taylor–Wiedemann, J. et al., "Monocytes are a major site of persistence of human cytomegalovirus in peripheral blood mononuclear cells," J. Gen. Virol. 72:2059–64.

van der Bij, W., "Rapid immunodiagnosis of active cytomegalovirus infection monoclonal antibody staining of blood leucocytes," *J Med. Virol.* 25:179–88 (1988).

Walmsley, S.L. et al., "Treatment of cytomegalovirus retinitis with trisodium phosphonoformate hexahydrate (Foscarnet)," *J. Infect. Dis.* 157(3):569–72 (1988).

Whitley, R.J. and Gnann, J.W., Jr., "Acyclovir: a decade later," *New Engl. J. Med.* 327(11):782–9 (1992).

Yamashiroya, H.M. et al., "Hepesviriae in the coronary arteries and aorta young trauma victims," *Am. J. Path.* 130(1):71–9 (1988).

```
  1 ATGCGGGGTTCTCATCATCATCATCATCATGGTATGGCTAGCATGACTGGTGGACAGCAA    60
  1   M  R  G  S  H  H  H  H  H  H  G  M  A  S  M  T  G  G  Q  Q    20

61 ATGGGTCGGGATCTGTACGACGATGACGATAAGGATCGATGGATCCGACCTCGAGATCCG   120
 21   M  G  R  D  L  Y  D  D  D  D  K  D  R  W  I  R  P  R  D  P    40

[pp65 ->
121 GCTTTTACCTCACACGAGCATTTTGGGCTGCTGTGTCCCAAGAGCATCCCGGGCCTGAGC   180
 41   A  F  T  S  H  E  H  F  G  L  L  C  P  K  S  I  P  G  L  S    60

181 ATCTCAGGTAACCTATTGATGAACGGGCAGCAGATCTTCCTGGAGGTGCAAGCGATACGC   240
 61   I  S  G  N  L  L  M  N  G  Q  Q  I  F  L  E  V  Q  A  I  R    80

241 GAGACCGTGGAACTCCGTCAGTACGATCCCGTGGCTGCGCTCTTCTTTTTCGATATCGAC   300
 81   E  T  V  E  L  R  Q  Y  D  P  V  A  A  L  F  F  F  D  I  D   100

301 TTGCTGCTGCAGCGCGGGCCTCAGTACAGCGAACACCCCACCTTCACCAGCCAGTATCGC   360
101   L  L  L  Q  R  G  P  Q  Y  S  E  H  P  T  F  T  S  Q  Y  R   120

361 ATCCAGGGCAAGCTTGAGTACCGACACACCTGGGACCGGCACGACGAGGGTGCCGCCCAG   420
121   I  Q  G  K  L  E  Y  R  H  T  W  D  R  H  D  E  G  A  A  Q   140

421 GGCGACGACGACGTCTGGACCAGCGGATCGGACTCCGACGAGGAACTCGTAACCACCGAG   480
141   G  D  D  D  V  W  T  S  G  S  D  S  D  E  E  L  V  T  T  E   160

481 CGCAAGACGCCCCGCGTTACCGGCGGCGGCGCCATGGCGGGCGCCTCCACTTCCGCGGGC   540
161   R  K  T  P  R  V  T  G  G  G  A  M  A  G  A  S  T  S  A  G   180

541 CGCAAACGCAAATCAGCATCCTCGGCGACGGCGTGCACGGCGGGCGTTATGACACGCGGC   600
181   R  K  R  K  S  A  S  S  A  T  A  C  T  A  G  V  M  T  R  G   200

<- pp65]
601 CGCCTTAAGGCCGAGTCCACCGTCGCGCCCGAAGAGGACACCGACGAGGATTCCGACAAC   660
201   R  L  K  A  E  S  T  V  A  P  E  E  D  T  D  E  D  S  D  N   220

[p38 ->
661 GGATCTGCAGCTGGTACCATGGAATTCGCGGACTACGTGGATCCCCATTATCCCGGGTGG   720
221   G  S  A  A  G  T  M  E  F  A  D  Y  V  D  P  H  Y  P  G  W   240

721 GGTCGGCGTTACGAGCCCGCGCCGTCTTTGCATCCGTCTTATCCCGTGCCGCCGCCACCA   780
241   G  R  R  Y  E  P  A  P  S  L  H  P  S  Y  P  V  P  P  P  P   260

781 TCACCGGCCTATTACCGTCGGCGCGACTCTCCGGGCGGTATGGATGAACCACCGTCCGGA   840
261   S  P  A  Y  Y  R  R  R  D  S  P  G  G  M  D  E  P  P  S  G   280

841 TGGGAGCGTTACGACGGTAGTCACCGTGGTCAGTCGCAGAAGCAGCACCGTCACGGGGGC   900
281   W  E  R  Y  D  G  S  H  R  G  Q  S  Q  K  Q  H  R  H  G  G   300

901 AGCGGCGGACACAACAAACGCCGTAAGGAAGCCGCGGCGGCGTCGTCGTCCTCGGAGACA   960
301   S  G  G  H  N  K  R  R  K  E  A  A  A  A  S  S  S  S  E  T   320

961 GACTTGAGTTTCCCCGGCGAGGCCGAGCACGGCCGGGCGCGAAAGCGTCTAAAAAGTCAC  1020
321   D  L  S  F  P  G  E  A  E  H  G  R  A  R  K  R  L  K  S  H   340

1021 GTCAATAGCGACGGTGGAAGTGGCGGGCACGTGGGTTCCAATCAGCAGCAGCAACAACGT 1080
341   V  N  S  D  G  G  S  G  G  H  V  G  S  N  Q  Q  Q  Q  Q  R   360

1081 TACGATGAACTGCGGGATGCCATTCACGAGCTGAAACGCGATCTGTTTGCTGCGCGGCAG 1140
361   Y  D  E  L  R  D  A  I  H  E  L  K  R  D  L  F  A  A  R  Q   380
```

FIG. 1A.: DNA and amino acid sequence of the combined antigen

```
1141 AGTTCTACGTTACTTTCGGCGGCTCTTCCCGCTGCGGCCTCTTCCTCCCCGACTACTACT 1200
 381   S   S   T   L   L   S   A   A   L   P   A   A   A   S   S   S   P   T   T   T   400

1201 ACCGTGTGTACTCCCACCGGCGAGCTGACGAGCGGCGGAGGAGAAACACCGACGGCACTT 1260
 401   T   V   C   T   P   T   G   E   L   T   S   G   G   E   T   P   T   A   L   420

1261 CTATCAGGAGGTGCCAAGGTAGCTGAGCGCGCTCAGGCCGGTGTGGTGAACGCCAGTTGC 1320
 421   L   S   G   G   A   K   V   A   E   R   A   Q   A   G   V   V   N   A   S   C   440

1321 CGCCTCGCTACCGCGTCGGGTTCTGAGGCGGCAACGGCAGGGCCTTCGACGGCGGGTTCT 1380
 441   R   L   A   T   A   S   G   S   E   A   A   T   A   G   P   S   T   A   G   S   460

1381 TCTTCCTGCCCGGCTAGTGTCGTGTTAGCCGCCGCTGCTGCCCAAGCCGCCGCAGCTTCC 1440
 461   S   S   C   P   A   S   V   V   L   A   A   A   A   Q   A   A   A   A   S   480

<- p38)        (pp150 ->
1441 CAGAGCCCGCCCAAAGACATGGTGGAATTCGAAGCTTTGGTAGGTCGACCGCCCTCGGTC 1500
 481   Q   S   P   P   K   D   M   V   E   F   E   A   L   V   G   R   P   P   S   V   500

1501 CCCGTGAGCGGTAGCGCGCCGGGTCGCCTGTCCGGCACCAGCCGGGCCGCCTCGACCACG 1560
 501   P   V   S   G   S   A   P   G   R   L   S   G   T   S   R   A   A   S   T   T   520

1561 CCGACGTATCCCGCGGTAACCACCGTTTACCCACCGTCGTCTACGGCCAAAAGCAGCGTA 1620
 521   P   T   Y   P   A   V   T   T   V   Y   P   P   S   S   T   A   K   S   S   V   540

1621 TCGAATGCGCCGCCTGTGGCCTCCCCCTCCATCCTGAAACCGGGGGCGAGCGCGGCTTTG 1680
 541   S   N   A   P   P   V   A   S   P   S   I   L   K   P   G   A   S   A   A   L   560

1681 CAATCACGCCGCTCGACGGGGACCGCCGCCGTAGGTTCCCCCGTCAAGAGCACGACGGGC 1740
 561   Q   S   R   R   S   T   G   T   A   A   V   G   S   P   V   K   S   T   T   G   580

1741 ATGAAAACGGTGGCTTTCGACCTATCGTCGCCCCAGAAGAGCGGTACGGGGCCGCAACCG 1800
 581   M   K   T   V   A   F   D   L   S   S   P   Q   K   S   G   T   G   P   Q   P   600

1801 GGTTCTGCCGGCATGGGGGGCGCCAAAACGCCGTCGGACACCGTGCAGAACATCCTCCAA 1860
 601   G   S   A   G   M   G   G   A   K   T   P   S   D   T   V   Q   N   I   L   Q   620

<- pp150)
1861 AAGATCGAGAAGATTAAGAACACGGAGGAAGCTTGA
 621   K   I   E   K   I   K   N   T   E   E   A   *
```

FIG. 1B

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 28 base pairs
( B ) TYPE: nucleic acid
( C ) STRANDEDNESS: single (D) TOPOLOGY: linear (i i) MOLECULE TYPE: cDNA (x i) SEQUENCE DESCRIPTION: SEQ ID NO:1:

GGGTGAATTC CAGTTGGCGG CACGTCAC                                28

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:2:

CGCGGAATTC TTTATTAGGG TATCACGGTA G                            31

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:3:

TGAGTGAATT CGCGGACTAC GTGGATCCCC                              30

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:4:

AGCTTGAATT CCACCATGTC TTTGGGCGG                               29

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:5:

CTGGATCCGG CTTTTACCTC ACACG                                   25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:6:

TGGGATCCCG TTGTCGGAAT CCTCG　　　　　　　　　　　　　　　　　　　　　　　　25

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGGTCAAGCT TCGTCGGTGT TCCTTCCTTG　　　　　　　　　　　　　　　　　　　　　30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CCGTCAAGCT TTCCCGACAC GTCACTATCC　　　　　　　　　　　　　　　　　　　　　30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TGGCAAAGCT TTGGTAGGTC GACCGCCCTC　　　　　　　　　　　　　　　　　　　　　30

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TCGTCAAGCT TCCTCCGTGT TCTTAATCTT CTCG　　　　　　　　　　　　　　　　　　34

( 2 ) INFORMATION FOR SEQ ID NO:11:

( i ) SEQUENCE CHARACTERISTICS:
        ( A ) LENGTH: 1896 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ATGCGGGGTT CTCATCATCA TCATCATCAT GGTATGGCTA GCATGACTGG TGGACAGCAA　　60
ATGGCTCGCC ATCTGTACGA CCATGACGAT AACCATCGAT CCATCCCACC TCCACATCCG　120

-continued

| | | | | | |
|---|---|---|---|---|---|
|GCTTTTACCT|CACACGAGCA|TTTTGGGCTG|CTGTGTCCCA|AGAGCATCCC|GGGCCTGAGC|180|
|ATCTCAGCTA|ACCTATTGAT|GAACCCCCAC|CAGATCTTCC|TGCAGCTGCA|AGCGATACGC|240|
|GAGACCGTGG|AACTGCGTCA|GTACGATCCC|GTGGCTGCGC|TCTTCTTTTT|CGATATCGAC|300|
|TTGCTGCTGC|AGCGCCCCCC|TCAGTACAGC|GAACACCCCA|CCTTCACCAG|CCAGTATCGC|360|
|ATCCACCGCA|ACCTTCACTA|CCGACACACC|TGCCACCGCC|ACGACGAGCC|TGCCCCCCAC|420|
|CCCGACGACG|ACGTCTCGAC|CAGCCGATCC|CACTCCGACG|AGGAACTCGT|AACCACCCAG|480|
|CGCAAGACCC|CCCGCGTTAC|CGCCCGCGGC|GCCATGCCGG|GCCCCTCCAC|TTCCGCGGCC|540|
|CCCAAACGCA|AATCAGCATC|CTCGGCCACG|CCGTCCACCG|CGGGCGTTAT|GACACGCGGC|600|
|CCCCTTAAGC|CCCACTCCAC|CGTCGCGCCC|GAAGAGCACA|CCCACCAGGA|TTCCCACAAC|660|
|GGATCTGCAG|CTGGTACCAT|CGAATTCCCG|CACTACCTGG|ATCCCCATTA|TCCCCCGTGC|720|
|GCTCCGCGTT|ACGACCCCCC|CCCGTCTTTG|CATCCCTCTT|ATCCCGTGCC|GCCGCCACCA|780|
|TCACCGCCCT|ATTACCGTCG|GCGCGACTCT|CCGCCCGCTA|TGGATGAACC|ACCGTCCGGA|840|
|TGCGACCGTT|ACGACCGTAG|TCACCGTGCT|CAGTCGCAGA|AGCAGCACCG|TCACGCGCGC|900|
|AGCGGCGGAC|ACAACAAACG|CCGTAAGGAA|GCCGCGGCCG|CGTCGTCGTC|CTCGGAGACA|960|
|GACTTGAGTT|TCCCCGGCGA|GGCCGAGCAC|GGCCGGGCGC|GAAAGCGTCT|AAAAAGTCAC|1020|
|GTCAATAGCG|ACCGTCGAAG|TGGCGGGCAC|GTGGGTTCCA|ATCAGCAGCA|GCAACAACGT|1080|
|TACGATGAAC|TGCGGGATGC|CATTCACGAG|CTGAAACGCG|ATCTGTTTGC|TGCGCGGCAG|1140|
|AGTTCTACGT|TACTTTCGGC|GGCTCTTCCC|GCTGCGGCCT|CTTCCTCCCC|GACTACTACT|1200|
|ACCCTGTGTA|CTCCCACCGC|CGACCTCACG|ACCCCGGAC|GAGAAACACC|CACGCCACTT|1260|
|CTATCACCAG|CTCCCAACCT|ACCTCACCGC|GCTCAGGCCC|CTGTGCTGAA|CCCCAGTTGC|1320|
|CGCCTCGCTA|CCGCGTCGGG|TTCTGAGGCG|GCAACGGCAG|GGCCTTCGAC|GGCGGGTTCT|1380|
|TCTTCCTGCC|CGGCTACTCT|CCTGTTACCC|GCCGCTCCTC|CCCAACCCCC|CCCACCTTCC|1440|
|CAGAGCCCGC|CCAAAGACAT|GGTGGAATTC|GAAGCTTTGG|TAGGTCGACC|GCCCTCGGTC|1500|
|CCCGTGACCG|CTACCCCGCC|GGCTCGCCTG|TCCGCCACCA|CCCCCCCCGC|CTCGACCACG|1560|
|CCGACGTATC|CCGCGCTAAC|CACCCTTTAC|CCACCGTCCT|CTACGGCCAA|AACCACCGTA|1620|
|TCGAATGCGC|CGCCTGTGGC|CTCCCCCTCC|ATCCTGAAAC|CGGGGGCGAG|CGCGGCTTTG|1680|
|CAATCACGCC|GCTCGACGCG|GACCGCCCCC|GTACGTTCCC|CCGTCAACAC|CACGACCGGC|1740|
|ATCAAAACGC|TGGCTTTCGA|CCTATCGTCG|CCCCAGAACA|CCCCTACGGG|CCCGCAACCG|1800|
|GCTTCTCCCG|CCATGGGGCG|CGCCAAAACC|CCGTCGGACA|CCGTGCACAA|CATCCTCCAA|1860|
|AAGATCGACA|AGATTAAGAA|CACGGACGAA|GCTTGA| | |1896|

( 2 ) INFORMATION FOR SEQ ID NO:12:

( i ) SEQUENCE CHARACTERISTICS:
        ( A ) LENGTH: 631 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Met Arg Gly Ser His His His His His Gly Met Ala Ser Met Thr
                5                      10                  15

Gly Gly Gln Gln Met Gly Arg Asp Leu Tyr Asp Asp Asp Lys Asp
                20                    25                  30

Arg Trp Ile Arg Pro Arg Asp Pro Ala Phe Thr Ser His Glu His Phe
              35                      40                  45

```
Gly Leu Leu Cys Pro Lys Ser Ile Pro Gly Leu Ser Ile Ser Gly Asn
         50                  55                  60
Leu Leu Met Asn Gly Gln Gln Ile Phe Leu Glu Val Gln Ala Ile Arg
 65                  70                  75                   80
Glu Thr Val Glu Leu Arg Gln Tyr Asp Pro Val Ala Ala Leu Phe Phe
                 85                  90                       95
Phe Asp Ile Asp Leu Leu Leu Gln Arg Gly Pro Gln Tyr Ser Glu His
            100                 105                 110
Pro Thr Phe Thr Ser Gln Tyr Arg Ile Gln Gly Lys Leu Glu Tyr Arg
        115                 120                 125
His Thr Trp Asp Arg His Asp Glu Gly Ala Ala Gln Gly Asp Asp Asp
    130                 135                 140
Val Trp Thr Ser Gly Ser Asp Ser Asp Glu Glu Leu Val Thr Thr Glu
145                 150                 155                 160
Arg Lys Thr Pro Arg Val Thr Gly Gly Gly Ala Met Ala Gly Ala Ser
                165                 170                 175
Thr Ser Ala Gly Arg Arg Arg Lys Ser Ala Ser Ser Ala Thr Ala Cys
            180                 185                 190
Thr Ala Gly Val Met Thr Arg Gly Arg Leu Lys Ala Glu Ser Thr Val
        195                 200                 205
Ala Pro Glu Glu Asp Thr Asp Glu Asp Ser Asp Asn Gly Ser Ala Ala
    210                 215                 220
Gly Thr Met Glu Phe Ala Asp Tyr Val Asp Pro His Tyr Pro Gly Trp
225                 230                 235                 240
Gly Arg Arg Tyr Glu Pro Ala Pro Ser Leu His Pro Ser Tyr Pro Val
                245                 250                 255
Pro Pro Pro Pro Ser Pro Ala Tyr Tyr Arg Arg Arg Asp Ser Pro Gly
            260                 265                 270
Gly Met Asp Glu Pro Pro Ser Gly Trp Glu Arg Tyr Asp Gly Ser His
        275                 280                 285
Arg Gly Gln Ser Gln Lys Gln His Arg His Gly Gly Ser Gly Gly His
    290                 295                 300
Asn Lys Arg Arg Lys Glu Ala Ala Ala Ala Ser Ser Ser Ser Glu Thr
305                 310                 315                 320
Asp Leu Ser Phe Pro Gly Glu Ala Glu His Gly Arg Ala Arg Lys Arg
                325                 330                 335
Leu Lys Ser His Val Asn Ser Asp Gly Gly Ser Gly Gly His Val Gly
            340                 345                 350
Ser Asn Gln Gln Gln Gln Gln Arg Tyr Asp Glu Leu Arg Asp Ala Ile
        355                 360                 365
His Glu Leu Lys Arg Asp Leu Phe Ala Ala Arg Gln Ser Ser Thr Leu
    370                 375                 380
Leu Ser Ala Ala Leu Pro Ala Ala Ala Ser Ser Ser Pro Thr Thr Thr
385                 390                 395                 400
Thr Val Cys Thr Pro Thr Gly Glu Leu Thr Ser Gly Gly Gly Glu Thr
                405                 410                 415
Pro Thr Ala Leu Leu Ser Gly Gly Ala Lys Val Ala Glu Arg Ala Gln
            420                 425                 430
Ala Gly Val Val Asn Ala Ser Cys Arg Leu Ala Thr Ala Ser Gly Ser
        435                 440                 445
Glu Ala Ala Thr Ala Gly Pro Ser Thr Ala Gly Ser Ser Ser Cys Pro
    450                 455                 460
Ala Ser Val Val Leu Ala Ala Ala Ala Ala Gln Ala Ala Ala Ala Ser
```

| 465 | | | | | 470 | | | | | 475 | | | | | 480 |
|---|---|---|---|---|---|---|---|---|---|---|---|---|---|---|---|
| Gln | Ser | Pro | Pro | Lys 485 | Asp | Met | Val | Glu | Phe 490 | Glu | Ala | Leu | Val | Gly 495 | Arg |
| Pro | Pro | Ser | Val 500 | Pro | Val | Ser | Gly | Ser 505 | Ala | Pro | Gly | Arg | Leu 510 | Ser | Gly |
| Thr | Ser | Arg 515 | Ala | Ala | Ser | Thr | Thr 520 | Pro | Thr | Tyr | Pro | Ala 525 | Val | Thr | Thr |
| Val | Tyr 530 | Pro | Pro | Ser | Ser | Thr 535 | Ala | Lys | Ser | Ser | Val 540 | Ser | Asn | Ala | Pro |
| Pro 545 | Val | Ala | Ser | Pro | Ser 550 | Ile | Leu | Lys | Pro | Gly 555 | Ala | Ser | Ala | Ala | Leu 560 |
| Gln | Ser | Arg | Arg | Ser 565 | Thr | Gly | Thr | Ala | Ala 570 | Val | Gly | Ser | Pro | Val 575 | Lys |
| Ser | Thr | Thr | Gly 580 | Met | Lys | Thr | Val | Ala 585 | Phe | Asp | Leu | Ser | Ser 590 | Pro | Gln |
| Lys | Ser | Gly 595 | Thr | Gly | Pro | Gln 600 | Pro | Gly | Ser | Ala | Gly | Met 605 | Gly | Gly | Ala |
| Lys | Thr 610 | Pro | Ser | Asp | Thr | Val 615 | Gln | Asn | Ile | Leu | Gln 620 | Lys | Ile | Glu | Lys |
| Ile 625 | Lys | Asn | Thr | Glu | Glu 630 | Ala | | | | | | | | | |

HUMAN CYTOMEGALOVIRUS ANTIGEN AND ITS USE

FIELD OF THE INVENTION

The present invention relates to the field of virology, specifically, human cytomegalovirus and the immune response to this infection.

BACKGROUND OF THE INVENTION

Human cytomegalovirus (HCMV) belongs to the herpes virus family. Infection with HCMV occurs frequently, as evidenced by the high percentage (over 50%) of adults having antibodies to this virus. Infection in the normal immunocompetent individual is mild or asymptomatic. However, in newborns and in the immunocompromised host such as organ and bone marrow transplant recipients and AIDS patients, severe disease develops (reviewed by Ho (1991) in: Cytomegalovirus: Biology and infection, (2nd ed.), Plenum Med. Press, New York).

Like other herpes viruses, HCMV can establish a life-long latency after initial infection (Stevens (1989) Microbiol. Rev. 53:318–332; Bruggeman (1993) Virchows Arch, B cell Pathol. 64:325–333). The site of latency is unknown. There are some data indicating that several organs and tissues such as kidney, heart and vessel wall of large vessels are sites of latency. In addition, blood cells such as macrophages can contain latent virus (Hendrix et al. (1989) Am. J. Pathol. 134:1151–1157; Yomashiroya et al. (1988) Am. J. Pathol. 130:71–79; Tanake et al. (1992) J. Vasc. Surg. 16:274–279; Stanier et al. (1989) Br. Med. J. 299:897–898; Bevan et al. (1991) Br. J. Haematol. 78:94–99; Taylor-Wiedeman et al. (1991) J. Gen. Virol. 72:2059–2064).

From the latent infection the virus can reactivate resulting in an endogenous infection posing a risk in the immunodeficient host. Both primary infections and reinfections (either endogenous, by reactivation of latent virus within the host or exogenous, by reinfection with a new virus from outside) can lead to acute (or active) infection. Especially primary infections can result in life-threatening disease (Rubin (1990) Rev. Infect. Dis. 12(suppl.7):S754–S766; Schooley (1990) Rev. Infect. Dis. 12(suppl.7):S811–S819).

Although the cellular immunity is the most important part of the immune response for clearing or reducing HCMV infection in the host, it is clear from studies in humans and in animal models that also humoral immunity has an effect on the course of the infection by reducing or preventing the CMV-associated symptoms (Meyers et al. (1983) Ann. Intern. Med. 98:442–446; Snijdman et al. (1987) New Engl. J. Med. 317:1049–1054; Stals et al. (1994) Antiviral Res. 25:147–160).

Recently, experiments in animal models have shown that clinical symptoms can be prevented by vaccination, supporting the finding that the presence of antibodies reduce CMV infection and, as a consequence, disease.

Although antiviral chemotherapy has been successful for some herpes viruses, especially for herpes simplex viruses, the prevention and treatment of HCMV infection remain difficult. The best results for HCMV therapy are obtained when the therapy is started very early in infection (Whitley & Gnann (1992) New Engl. J. Med. 327:782–789; Meyers et al. (1988) New Engl. J. Med. 318:70–75; Collaborative DHPG treatment study group (1986) New Engl. J. Med. 314:801–806; Walmsley (1988) J. Infect. Dis. 157:569; Goodrich et al. (1991) New Engl. J. Med. 325:1601–1607; Merigan et al. (1992) New Engl. J. Med. 326:1182–1186).

Therefore, early detection of active HCMV infection is important. For the early detection of acute HCMV infection (either primary or reactivation of latent infection) there is an increasing need for new specific and sensitive techniques. Besides the detection of virus, viral antigens and viral genome, detection of anti-HCMV antibodies, especially IgM (and to a lesser extent IgA) is important (Landini (1993) Prog. Med. Virol. 4:157–177; Bij vd W et al. (1988) J. Med. Virol. 25:179–188; Genna et al. (1991) J. Inf. Dis. 164:488–498; Nielsen et al. (1980) J. Clin. Microbiol. 26:654–661; Sarov et al. (1982) Clin. Exp. Immunol. 48:321–328).

The present invention addresses the need for early detection of HCMV by providing a synthetic protein useful in an assay for the early detection of anti-HCMV antibodies. The present invention further provides a HCMV vaccine.

BRIEF SUMMARY OF THE INVENTION

The invention features a human cytomegalovirus protein, also called a "combined antigen", having at least three HCMV protein epitopes, useful as a HCMV vaccine and in an assay for early detection of HCMV infection. The invention further features a method of preparing the combined antigen of the invention by recombinant DNA techniques.

In a specific embodiment, the combined antigen of the invention is a fusion protein having the amino acid sequence of SEQ ID NO:12. In this embodiment, the combined antigen is composed of six histidine residues and defined portions of the HCMV proteins UL32, UL83 and UL80. The type or the number of HCMV antigens included in the "combined" antigen is not limited, and may include more than three epitopes. The antigens (epitopes) used in this assay show an enhanced ability to bind IgM, exhibiting a 2- to 3-fold increase in IgM antibody binding relative to a single antigen.

Included in the invention are nucleotide sequences which encode the combined antigen of the invention. These nucleotide sequences include DNA, CDNA and RNA sequences encoding the combined antigen of the invention. In a specific embodiment, the invention includes nucleotide sequences having the nucleotide sequence of SEQ ID No:11. It is also understood that the nucleotide sequences of the invention include minor modifications of the nucleotide sequences encoding the combined antigen of the invention, so long as the resulting proteins have the same in vitro and/or in vivo activity and function of the protein encoded by the sequence of SEQ ID NO:11.

The invention further includes vectors containing the nucleotide sequences of the invention and host cells transformed with the vectors of the invention.

The present invention features an assay for detecting the presence and the amount of antibodies to HCMV-encoded antigens in tissue and biological fluid of infected humans. This assay achieves improved sensitivity of immunodetection by combining the immuno-dominant regions of early-formed proteins into a single protein. In addition, the combined antigen of the invention can be attached to a solid phase for use in a solid phase assay such as an immunoassay or similar assays widely used for detecting both antigen and antibodies (IgG, IgM and IgA) in body samples. The enhanced ability of the combined antigen of the invention to bind HCMV-specific antibodies provides a sensitive assay able to detect HCMV-mediated diseases at an early stage of infection, thus allowing early treatment to commence.

In one aspect, the invention features use of the combined antigen as a human cytomegalovirus vaccine. The combined antigen useful as a vaccine contains portions of the proteins encoded by HCMV sequences ppUL32, ppUL80 and ppUL83, made as described below. The vaccine of the invention is useful in conferring protective immunity in human subjects at risk for a HCMV-mediated disease.

These and other objects, advantages, and features of the invention will become apparent to those persons skilled in the art upon reading the details of the methods, assays, and peptides of the invention as more fully described below.

BRIEF DESCRIPTION OF THE DRAWING

FIGS. 1A and 1B show the nucleic acid sequence and corresponding amino acid sequence of the exemplary combined antigen of the invention.

DETAILED DESCRIPTION

Before the present proteins, assays, and methods of use are described, it is to be understood that this invention is not limited to particular methods, assays, or proteins described, as such methods, assays and proteins may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Combined Antigen

The present invention features a "combined antigen" having a portions of the amino acid sequences of the Towne strain of human cytomegalovirus. By the term "combined antigen" is meant a non-naturally occurring protein comprising in a single amino acid chain, all or an immunogenic part of the amino acid sequences of the proteins encoded by UL32 (ppUL32), UL80 (ppUL80), and UL83 (ppUL83). These amino acid sequences define epitopes which react efficiently with human immunoglobulins. The naturally occurring intact UL32 protein encodes a basic phosphoprotein of 150 kDa which binds serum from HCMV-infected patients. UL83 and UL80 encode the major HCMV matrix protein and assembly protein, respectively. The combined antigen protein of the invention binds HCMV-specific IgM with a 2-to 3-fold increased affinity relative to the naturally-occurring single epitope. The combined antigen of the invention has the amino acid sequence of SEQ ID NO:12.

By "enhanced ability to bind" or "increased binding affinity" is meant an improved binding of the combined antigen of the invention to HCMV-specific antibodies relative to a single epitope. Thus, the presence of the multiple epitopes in a single molecule provide a synergistic effect on binding to HCMV-specific antibodies. The terms "synergistic", "synergistic effect" and the like are used herein to describe improved binding to HCMV-specific antibodies of the combined antigen of the invention relative to a single epitope. Although a synergistic effect in some fields means an effect which is more than additive (e.g., 1+1=3), in the medical field a synergistic effect may be additive (1+1=2) or less than additive (1+1=1.6). Thus, the presence of multiple antigenic domains in a single molecule is considered to provide a synergistic effect on HCMV-specific antibody binding (e.g., >1.0) relative to a single domain (1.0).

The combined antigen of the invention is comprised of antigenic domains from proteins from the HCMV Towne strain which can efficiently detect anti-HCMV antibodies in biological samples. The combined antigen of the invention is further comprised of a 6 histidine residue tag used to purify the antigen. The histidine tag is not immunogenic and does not interfere with antibody detection.

The invention includes nucleotide sequences encoding the combined antigen of the invention. These nucleotide sequences can be expressed in either prokaryote or eukaryote host cells, including microbial, yeast, insect and mammalian organisms. Methods of expressing DNA sequences are known in the art. Biologically functional viral and plasmid DNA vectors capable of expression and replication in a host are known in the art. Such vectors are used to incorporate DNA sequences of the invention.

Transformation of a host cell with vectors containing DNA encoding the combined antigen of the invention may be carried out by conventional techniques as are well known to those skilled in the art. Such transformed host cells are capable of expressing the combined antigen. Isolation and purification of the expressed combined antigen may be carried out by conventional means well known in the art.

Assay Method for the Detection of HCMV Antibodies

The combined antigen of the present invention possesses advantages over prior art antigen preparations, including 2- to 3-fold improved binding to IgM antibodies. This improved IgM binding provides a more accurate and sensitive assay for the detection of HCMV antibodies present during early HCMV-mediated infection of a human subject.

By "HCMV-sediated infection" or "HCMV-mediated disease" is meant any pathological condition resulting from infection of a human with human cytomegalovirus, including congenital infections.

Those skilled in the development of immuno-reactive techniques will understand that there are numerous well known procedures for the detection of antibodies and uses of antigens for this purpose. Thus while only a few assay methods are described herein, the invention is not limited to those assays specifically described. Included in the detection assay of the invention are both competitive and non-competitive assay methods. Examples of assays methods in which the combined antigen of the invention can be used include radio-immuno-assay (RIA), western blotting, enzyme linked immunosorbent assay (ELISA) and indirect immunofluorescence (IF) assays.

For the detection of acute HCMV infections two approaches are possible. The first is based on the detection of virus or parts of it (antigens or genome). Although in general this approach gives good results, it needs specific equipment and knowledge and can usually only be applied in academic centers or large laboratories.

The second approach is based on the detection of IgM antibodies in serum of the patient and on a rise in IgG class antibodies. Detection of antibodies can easily be accomplished using techniques such as the ELISA technique. In principle, this technique is relatively simple to handle and can be used in routine laboratories (Kraat et al. (1992) J.

Clin. Microbiol. 30:522–524; Lazzaroto et al. (1992) J. Clin. Lab. Anal. 6:216–218; Stagno et al. (1985) J. Clin. Microbiol. 21:930–935; Smith & Shelley (1988) J. Virol. Meth. 21:87–96; Marsano et al. (1990) J. Inf. Dis. 161:454–461).

Although from a theoretical point of view ELISA is a simple technique for IgM antibody detection, there are a lot of problems associated with the use of commercial ELISA kits. Currently available CMV-IgM antibody detection methods suffer from considerably variations in specificity and sensitivity. This is largely due to differences in antigen composition and the lack of antigen standardization.

These problems are solved by combining three recombinant viral proteins (ppUL80 (p38), ppUL83 (pp65) and ppUL32 (ppl150)) into a single synthetic protein suitable for detection of IgM antibodies. These viral proteins were employed to develop a sensitive method for early detection of acute HCMV infections in patients "at risk" such as organ recipients, premature infants and patients suffering from the acquired immunodeficiency syndrome (AIDS).

Human Cytomegalovirus Vaccine

Vaccination with inactivated or attenuated organisms or their products has been shown to be an effective method for increasing host resistance and ultimately has led to the eradication of certain common and serious infectious diseases. The use of vaccines is based on the stimulation of specific immune responses within a host.

The combined antigen described in this invention generates an immune response. The term "immune response" refers to a cytotoxic T cell response or increased serum levels of antibodies specific to an antigen, or to the presence of neutralizing antibodies to an antigen. The immune response is preferably sufficient to make the combined antigen of the invention useful as a vaccine for protecting human subjects from human cytomegalovirus infection. Additionally, antibodies generated by the combined antigen of the invention can be extracted and used to detect a virus in a body fluid sample. The term "protection" or "protective immunity" refers herein to the ability of the serum antibodies and cytotoxic T cell response induced during immunization to protect (partially or totally) against a disease caused by an infectious agent, e.g., human cytomegalovirus. The use of the combined antigen as a vaccine is expected to provide protective immunity to humans against severe HCMV infection by inducing antibodies against HCMV which are known to prevent severe clinical symptoms.

The invention includes a method of providing an immune response and protective immunity to a human against human cytomegalovirus-mediated diseases. The method includes administering the combined antigen of the invention to a human. The combined antigen of the invention is preferably administered as a formulation comprising a physiologically acceptable carrier and an effective amount of the combined antigen. A variety of physiologically acceptable carriers are known in the art, including for example, saline. Routes of administration, amounts, and frequency of administration are known to those skilled in the art for providing protective immunity to a recipient subject. Routes of administration include any method which confers protective immunity to the human recipient, including, but not limited to, inhalation, intravenous, intramuscular, intraperitoneal, intradermal, and subcutaneous. Preferably the combined antigen of the invention is provided to a human subject by subcutaneous or intramuscular injection. A range of amounts and frequency of administration is acceptable so long as protective immunity of the recipient is achieved. For example, 5 to 20 μg can be administered by intramuscular injection between 2 to 4 times over a three month period.

EXAMPLES

The following examples are put forth so as to provide those of ordinary skill in the art with a complete disclosure and description of how to make and use the assays of the invention, and are not intended to limit the scope of what the inventors regard as their invention. Efforts have been made to ensure accuracy with respect to numbers used (e.g., amounts, temperatures, etc.) but some experimental error and deviations should be accounted for. Unless otherwise indicated, temperature is in degrees Centigrade, molecular weight is average molecular weight, and pressure is at or near atmospheric.

Example 1

Construction of a vector which expresses part of ppUL80 from HCMV (Towne strain) as a fusion with six histidines.

Bacterial strains. All DNA cloning studies were done using *Escherichia coli* strain DH5α. Protein expression experiments were performed with *E. coli* BL21 (DE3) plysS.

Protein expression and purification. Bacteria were grown in TB medium containing ampicillin and chloramphenicol to an $OD_{600}$ of 1.0, after which protein expression was induced by addition of isopropyl-β-D-thiogalactopyranoside (IPTG) at 0.1 mM. One-step affinity chromatography of 6 histidine (6H) fusion proteins over Ni2+-chelating sepharose (Probond, Invitrogen) was carried out essentially as described by the manufacturers of the column material. Immunoblotting and ELISA experiments were conducted using standard techniques.

DNA fragment. The DNA fragment that encodes part of the ppUL80 protein of HCMV (Towne strain) was generated by PCR amplification. To develop oligonucleotides for PCR, we first had to determine the DNA sequence of part of the UL80 gene of the Towne strain. To this purpose, two oligonucleotides were generated which are homologous to UL80 sequences of the AD169 strain of HCMV. These oligonucleotides are of the sequence:

5'-GGGTGAATTCCAGTTGGCGGCACGTCAC-3' (ppUL80-N-EI) (SEQ ID NO:1) and

5'-CGCGGAATTCTTTATTAGGGTATCACGGTAG-3' (ppUL80-C-EI) (SEQ ID NO:2).

The sequences in bold print are identical to HCMV AD169 nucleotides 116475 to 116493 for ppUL80-N-EI, and complementary to nucleotides 117363 to 117386 for ppUL80-C-EI. The sequences in italics represent a recognition site for restriction endonuclease EcoRI. The oligonucleotides were used in PCR (1 cycle: 5 min at 94° C.; 30 cycles: 1 min at 94° C., 1 min at 55°C., 1 min at 72° C.; 1 cycle: 10 min at 72° C.) with DNA from the HCMV Towne strain as template. The resulting PCR product was cloned and sequenced. Based on this sequence, Towne strain-specific oligonucleotides were designed which were employed to amplify part of the Towne UL80 gene. To facilitate cloning, EcoRI restriction endonuclease cleavage sites were introduced in the DNA primers; these EcoRI sites are indicated below in italics. The sequences of the primers are:

5'-TGAGTGAATCGCGGACTACGTGGATCCCC-3' (ppUL80-N2-EI) (SEQ ID NO:3) and

5'-AGCTTGAATTMCACCATGTCTTTGGGCGG-3' (ppUL80-C2-EI) (SEQ ID NO:4)

The nucleotides in bold print correspond to HCMV AD169 nucleotides 116497 to 116515 for ppUL80-N2-EI and nucleotides 117259 to 117278 for ppUL80-C2-EI. After amplification, the PCR product was purified, digested with EcoRI and cloned into the EcoRI site of vector pRSET B (Invitrogen). In the resulting plasmid, the UL80 gene fragment is present at the 3' end of and in-frame with a fragment encoding six histidines (6H).

Example 2
Construction of a vector which expresses part of ppUL83 from HCMV (Towne strain) as a fusion with 6 histidines.

The DNA fragment that encodes part of the ppUL83 protein of HCMV (Towne strain) was generated by PCR. Oligonucleotides were developed which are homologous to the sequence of the Towne UL82 gene (Pande et al. (1991) Virology 182:220–228). BamHI restriction endonuclease cleavage sites were introduced in the DNA primers; these sites are indicated below in italics. The sequences of the primers are:

5'-CTGGATCCGGCTTTTACCTCACACG-3' (ppUL83-N-BI) (SEQ ID NO:5) and

5'-TGGGATCCCGTTGTCGGAATCCTCG-3' (ppUL83-C-BI) (SEQ ID NO:6)

The sequences in bold print of ppUL83-N-BI are identical to nucleotides 855 to 871 of the ppUL83 gene sequence. The bold sequence of ppUL83-C-BI is complementary to nucleotides 1380 to 1396 of the ppUL83 gene sequence. After PCR amplification, the PCR-product was purified, digested with BamHI and cloned into the BglII site of vector pRSET C (Invitrogen). In the resulting plasmid, the UL82 gene fragment is present at the 3' end of and in-frame with a fragment encoding 6H.

Example 3
Construction of a vector which expresses part of ppUL32 from HCMV (Towne strain) as a fusion with 6H.

The DNA fragment that encodes part of the ppUL32 protein of HCMV (Towne strain) was generated by PCR, similarly as described for cloning of part of the UL80 gene (see above). Oligonucleotides for PCR were only developed after sequencing part of the UL32 gene of the Towne strain. To this purpose, two oligonucleotides were generated which are homologous to UL32 sequences of the AD169 strain of HCMV. The sequences of these oligonucleotides are:

5'-CGGTCAAGCTTCGTCGGTGTTCCTTCCTTG-3' (ppUL32-N-HIII) (SEQ ID NO:7) and

5'-CCGTCAAGCTTTCCCGACACGTCACTATCC-3' (ppUL32-C-HIII) (SEQ ID NO:8)

The sequences in italics represent HindIII cleavage sites. The sequences in bold print are complementary to HCMV AD169 nucleotides 40288 to 40306 for ppUL32-N-HIII, and identical to nucleotides 39783 to 39804 for ppUL32-C-HIII. PCR was carried out with DNA from the HCMV Towne strain as template. The resulting PCR product was cloned and sequenced. Based on this sequence, Towne strain-specific oligonucleotides were developed which were subsequently used to amplify part of the Towne UL32 gene. HindIII restriction endonuclease cleavage sites were introduced into the primers; these sites are shown in italics in the sequences below. The sequences of the primers are:

5'-TGGCAAAGCTTTGGTAGGTCGACCGCCCTC-3' (ppUL32-N2-HIII) (SEQ ID NO:9) and

5'-TCGTCAAGCIMCTCCGTGTTCTTAATCTTCTCG-3' (ppUL32-C2-HIII)(SEQ ID NO:10)

The nucleotides in bold print correspond to HCMV AD169 nucleotides 40244 to 40262 for ppUL32-N2-HIII and nucleotides 39850 to 39874 for ppUL32-C2-HIII. After amplification, the PCR product was purified, cleaved with HindIII and cloned into the HindIII site of vector pRSET B (Invitrogen). In the resulting plasmid, the UL32 gene fragment is present at the 3' end of and in-frame with a fragment encoding 6 histidines.

Example 4
Construction of a vector which expresses parts of ppUL83, ppUL80 and ppUL32 from HCMV (Towne strain) as in-frame fusions with 6H.

To generate a plasmid which expresses a fusion protein of 6H and parts of ppUL83, ppUL80 and ppUL32, the DNA fragments encoding ppUL80 and ppUL32 were inserted into the EcoRI and HindIII sites, respectively, of the plasmid which contains the 6H-ppUL83 open reading frame (see Example 2 above). The resulting nucleic acid construct contains an in-frame fusion of the 6H-ppUL83 open reading frame and parts of the ppUL80 and ppUL32 genes which were described above. The amino acid sequence (SEQ ID NO:12) corresponding to the nucleic acid construct of the combined antigen (SEQ ID NO:11) of the invention are shown in FIGS. 1A–1B.

Example 5
Sensitive Assay for HCMV Antibodies

The combined antigen can be used in an enzyme linked immunosorbent assay (ELISA) as an antigen adsorbed to a carrier solid phase or in a competition assay in which known specific antibodies compete with antibodies present in the patient's serum for the specific epitopes on the combined antigen. The combined antigen can also be conjugated to a detection system, such as enzymes to detect serum antibodies which may be present in the patient's serum. An important advantage provided by the use of the combined antigen of the invention is that there are equal molar amounts of each of these three immunodominant antigens simultaneously present in the detection system, resulting in the improved sensitivity of the present assay.

What is claimed is:

1. An antigen comprising, the amino acid sequence from amino acid residue number 41 to residue number 631 of SEQ ID NO: 12 and characterized by an ability to bind HCMV-specific antibodies with a 2- to 3-fold increased affinity relative to an HCMV protein selected from the group consisting of UL80, UL83, and UL32.

2. The antigen of claim 1, further comprising six histidine residues in series, at the N-terminus or C-terminus.

3. The antigen of claim 1, wherein said antigen is produced by expression of the nucleic acid sequence of SEQ ID NO:11 in a suitable host cell.

4. An assay device, comprising:
a support surface; and
an antigen bound to said surface, wherein the antigen comprises the amino acid sequence from amino acid residue number 41 to residue number 631 of SEQ ID NO: 12, and is characterized by an enhanced ability to bind HCMV-specific IgM with a 2- to 3-fold increased affinity relative to an HCMV protein selected from the group consisting of UL80, UL83, and UL32.

5. A method for detecting and quantifying human cytomegalovirus (HCMV)-specific antibodies in a sample of human body fluid or tissue, said method comprising:
a) obtaining a sample of human body fluid or tissue;
b) contacting said sample with an antigen, wherein said antigen comprises the amino acid sequence from amino acid residue number 41 to residue number 631 of SEQ ID NO: 12 characterized by an enhanced ability to bind HCMV-specific IgM with a 2- to 3-fold increased affinity relative to an HCMV protein selected from the group consisting of UL80, UL83, and UL32;
c) detecting the amount of the antigen bound to HCMV-specific antibodies, wherein the amount of bound antigen is indicative of the presence of HCMV-specific antibodies.

6. The method of claim 5, wherein said antigen is labelled.

7. A vaccine for conferring protective immunity against human cytomegalovirus-mediated diseases, said vaccine comprises the antigen of claim 1.

* * * * *